United States Patent
Xue et al.

(10) Patent No.: US 6,507,753 B1
(45) Date of Patent: Jan. 14, 2003

(54) METHOD AND APPARATUS TO DETECT ACUTE CARDIAC SYNDROMES IN SPECIFIED GROUPS OF PATIENTS USING ECG

(75) Inventors: Qiuzhen Xue, Germantown, WI (US); Shankara Bonthu Reddy, Cedarburg, WI (US); Basel Taha, Menomonee Falls, WI (US); Jonathan Alan Murray, Sussex, WI (US)

(73) Assignee: GE Marquette Medical Systems, Inc., Milwaukee, WI (US)

( * ) Notice: Subject to any disclaimer, the term of this patent is extended or adjusted under 35 U.S.C. 154(b) by 287 days.

(21) Appl. No.: 09/634,355

(22) Filed: Aug. 9, 2000

(51) Int. Cl.[7] .............................................. A61B 5/0452

(52) U.S. Cl. ........................ 600/517; 600/515; 128/923

(58) Field of Search ................................ 128/920, 923; 600/509, 515, 517

(56) References Cited

U.S. PATENT DOCUMENTS 5,724,983 A    3/1998   Griffith et al.
5,921,940 A    7/1999   Verrier et al.
6,171,256 B1 * 1/2001   Joo et al. ..................... 600/508

OTHER PUBLICATIONS

Macfarlane et al., "The Normal Electrocardiogram and Vectorcardiogram," Pergamon Press, Comprehensive Electrocardiology: Therory and Practice in Health and Disease, vol. 1, University of Glasgow, pp. 407–430.*

"ECG changes during myocardial ischemia. Differences between men and women," Dellborg et al., Journal of Electrocardiology 1994; 27 Suppl:42–5, abstract.*

Goettsch G et al: "Extension of the Hannover HES ECG diagnostic program module" Proceedings of the Computers in Cardiology Meeting. Leuven, Sep. 12–15, 1987, Washington, IEEE Comp. Soc. Press, US, vol. Meeting 14, Sep. 12, 1987, pp. 151–154, XP000092866 p. 151, left–hand column, line 42—right–hand column, line 12.

Boersma et al: "Improved electrocardiographic criteria for confirmation of acute myocardial infarction with application in pre–hospital thrombolysis" Computers in Cardiology 1995 Vienna, Austria Sep. 10–13, 1995, New York, NY, USA, IEEE, US, Sep. 10, 1995, pp. 725–728, XP010154525 ISBN: 0–7803–3053–6.

Article 52 (4) EPC—Diagnostic method practised on the human or animal body.

(List continued on next page.)

Primary Examiner—Kennedy Schaetzle
(74) Attorney, Agent, or Firm—Ziolkowski Patent Solutions Group, LLC; Peter J. Vogel; Carl B. Horton

(57) ABSTRACT

In order to reduce bias associated with conventional ECG analysis, the present invention provides a method and apparatus to improve diagnosis of acute cardiac syndromes (ACS), such as acute myocardial infarction and acute cardiac ischemia (unstable angina), in specified groups of patients using ECG signals and automatic detection analysis. Specific criteria are developed and utilized based on a prespecified group selection for the particular patient. After identifying group membership for the particular patient, ECG data are acquired from a patient experiencing ACS symptoms. Known criteria typically used for assessing ACS are then modified for the particular group membership. Such criteria significantly reduce the bias found in a baseline group for which the known criteria were established. The invention is particularly useful in identifying an ACS, and the type of ACS, in females under the age of 60 where it has been found that the current critical ST threshold is too high to consistently identify an ACS in this subgroup.

35 Claims, 4 Drawing Sheets

OTHER PUBLICATIONS

Adams Marh G et al: Frequency of silent myocardial ischemia with 12–lead ST segment monitoring in the coronary care unit: Are there sex–related differences? Heart & Lung; vol. 28, No. 2, Mar. 1999, pp. 81–86 XP001041296 pp. 82–83, sections Instruments and procedures: and "Definitions of Ischemia".

Vaccarino, V.; Parsons, L.; Every, NR; Barron HV; Krumholz, HM; For the National Registry of Myocardial Infarction 2 Participants, *The New England Journal of Medicine*, Sex–based differences in early mortality after myocardial infarction, vol. 341, No. 4, p. 217–225, Jul. 22, 1999.

Hochman, JS; Tamis, JE; Thompson, TD; Weaver, WD; White HD; Vandewerf F; Aylward P. Topol EJ, Califf, RM; For the global Use of Strategies to Open Occluded Coronary Arteries in Acute Coronary Syndromes 11b Investigators, *The New England Journal of Medicine*, p. 226–232, vol. 341, No. 4, Jul. 22, 1999.

Editorial, *The New England Journal of Medicine*, Studies of acute coronary syndromes in women—lessons for everyone p. 275, vol. 341, No. 4, Jul. 22, 1999.

Farkouh, ME; PA, Reeder, GS, Zinsmeister, AR; Evans, RW; Meloy, TD; Kopecky, SL; Allen, M; Allison, TG; Gibbons, RJ; and Gabriel, SE For the Chest Pain Evaluation in the Emergency Room (CHEER) Investigators, *The New England Journal of Medicine*, A clinical trial of a chest–pain observation unit for patients with unstable angina, p. 1882–1888, vo. 339, No. 26, Dec. 24, 1998.

Mahon, NG; McKenna, CJ; Codd, MB; O'Rorke, C; McCann, HA; Sugrue, DD; *The American Journal of Cardiology*, Gender differences in the management and outcome of acute myocardial infarction in unselected patients in the thrombolytic era, vol. 85, Apr. 15, 2000.

\* cited by examiner

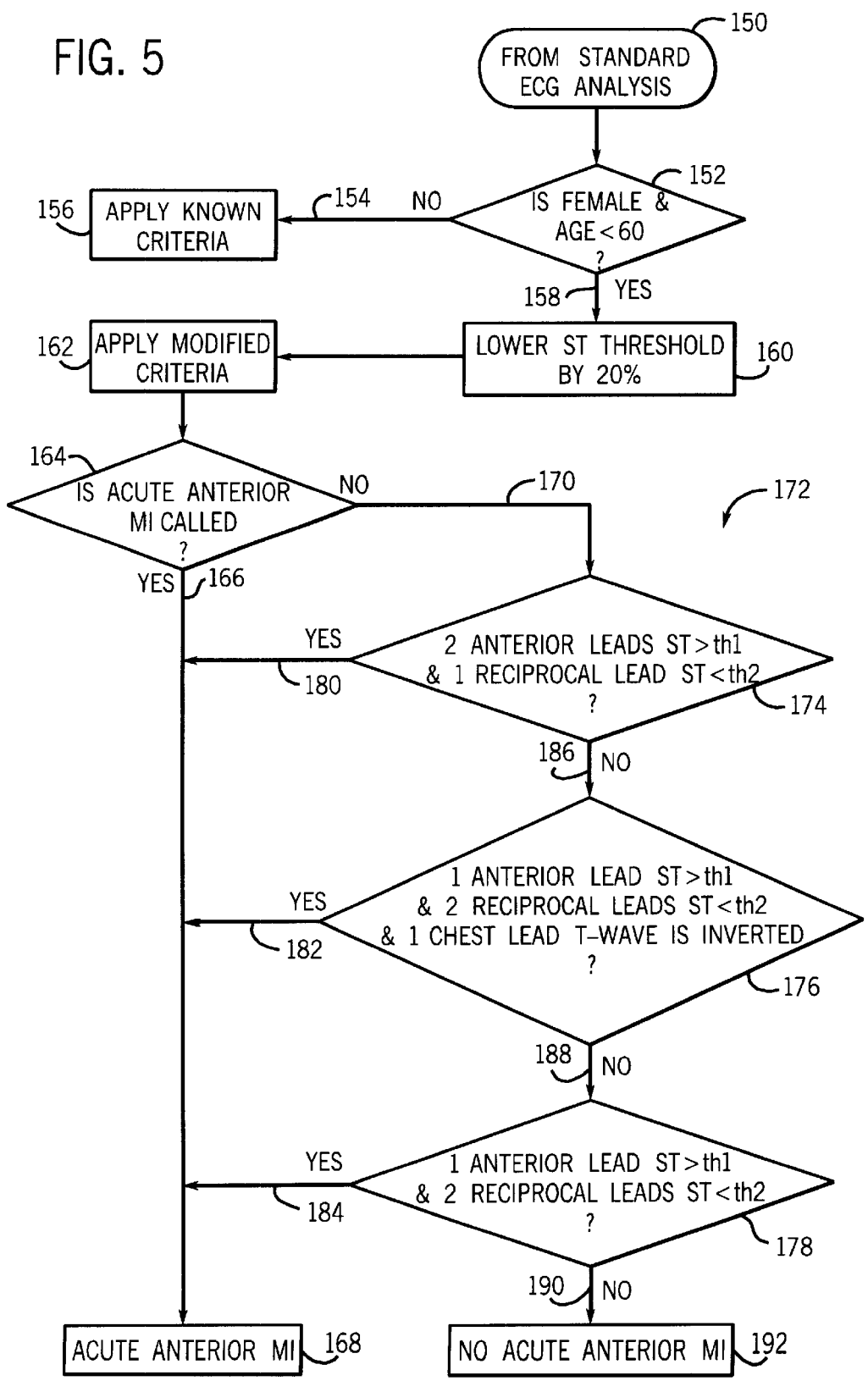

METHOD AND APPARATUS TO DETECT ACUTE CARDIAC SYNDROMES IN SPECIFIED GROUPS OF PATIENTS USING ECG

BACKGROUND OF THE INVENTION

The invention relates generally to electrocardiograms (ECGs) and the use thereof, and more particularly to, a method and apparatus to detect acute cardiac syndromes that is specific with respect to gender, age, height, weight, and/or race.

ECG analysis is a well established method for studying the function of the heart and identifying disorders of the heart. ECG is an important tool in diagnosing patients presented to an emergency room with chest pain. One particular disorder that is studied using ECG is acute cardiac syndromes (ACS), which includes, but is not limited to, acute myocardial infarction (MI) and acute cardiac ischemia (ACI), the latter of which is commonly referred to as unstable angina. Acute ischemia includes the starvation of oxygen to a portion of the heart, commonly caused by a partial blockage of the coronary arteries providing oxygenated blood to the heart, and acute infarction is due to the complete blockage of oxygen to a portion of the heart. Ischemia, or unstable angina, can lead to or be a symptom of infarction. It is well known that time is critical in diagnosing these conditions in a patient experiencing chest pain. Delay in diagnosis and therapy can result in serious impairment of the heart's function, including sudden death.

An ECG is a graphic tracing of the variations in the electrical potential caused by the excitation of the heart muscle and is detected at the body surface by an ECG device. The typical ECG is a scale or representation that shows deflections resulting from cardiac activity as changes in the magnitude of voltage and polarity over time and includes a P-Wave, a QRS complex, a T-Wave, and a U-Wave. These waves are then analyzed using a set of rules and parameters to determine what is normal and what is not. Certain deviations are used to flag a possible ACS.

However, recent studies indicate a significant difference in these "typical" clinical profiles, presentations, and outcomes between men and women with ACS that were not attributable to differences in baseline characteristics. Studies have shown that younger women have a higher mortality than older women, and men of all ages, following myocardial infarction. However, to date, these studies have not conclusively shown direct evidence that the findings might be attributed to pathophysiological and/or anatomical differences between men and women. For example, electrocardiographic evidence of acute MI conventionally includes the presence of ST elevations of at least 100 $\mu$V in two anatomically contiguous leads (a higher threshold of 200 $\mu$V is used for precordial leads). Since the previous studies used conventional, clinical criteria to assess the presence of acute MI and thereby determine the course of care for the patients, it is believed that the differences in mortality rates may be attributed, at least partially, to sub-clinical differences in the ST elevation levels on the admission ECG. If present, the sub-clinical differences in ST levels between symptomatic male and female patients (e.g., those complaining of chest pain) may be revealed only through more accurate computerized measurements of the ST levels from signal averaged (median) data. It is believed that these differences may have been obscured by the fact that development of conventional criteria for ECG ACS evidence was carried out through manual ST measurements on a baseline group that was largely male dominated or undifferentiated by gender, age, height, weight and race.

There are a number of computerized ECG analysis systems in the marketplace. However, it is generally believed that they all rely on a baseline group of patients that provides criteria that may be biased against certain groups of patients. It would therefore be advantageous to optimize the performance of computerized ACS criteria to more accurately detect such acute cardiac syndromes as acute MI and ACI for a patient falling within one group that does not necessarily have the same characteristics of the baseline group. For example, it is proposed herein that female patients under the age of 60 should have a lower ST elevation threshold than the male dominated group used as the traditional baseline. Therefore, it would be advantageous to improve the sensitivity for detection of acute MI/ACI for female patients while maintaining high specificity and, thus, eliminate the bias in the current criteria used.

SUMMARY OF THE INVENTION

A method and apparatus is disclosed to improve detection of acute cardiac syndromes (ACS) in specified groups of patients using ECG analysis to eliminate bias introduced by the current criteria that solves the aforementioned problems.

The invention includes the development and implementation of a computerized ACS criteria based analysis system to optimize performance for specified groups of patients. To develop the new criteria, a database of patient records is examined in which the patient records confirm the existence of ACS or the absence of ACS. That is, to ensure a bias neutral study, the presence or absence of ACS must be confirmed by a non-ECG diagnosis. For gender-based criteria, the database of admission ECGs divided into female and male groups. The difference of at least one ECG parameter is examined between the groups. In this example, the ECG parameter tested is the ST segment measurement of the ECG waveform. Either a fuzzy logic or a neural network can be used for pattern recognition in addition to classical pattern recognition methods such as linear discriminant function analysis and thresholding. After the differences are examined, a significance is assigned to the difference. Based on the significance assigned, the ECG-based automatic detection of ACS can be optimized for the specified subgroup.

In accordance with one aspect of the invention, a method of developing automatic detection of ACS using ECG signals includes examining a difference of at least one ECG parameter from patients in a baseline group that includes patients having ACS and those not having ACS, with patients in a second group that includes patients, also, having ACS and those not having ACS. After determining a significance of the differences examined, the method includes optimizing performance of ECG-based automatic detection of ACS for the second group of patients based on the significance determined. In a preferred embodiment, the ECG parameter is ST elevation. Since it has been found herein that female patients have a lower critical ST elevation than the baseline, male dominated group, the invention includes lowering the threshold level of the ST elevation parameter in the ECG analysis.

In accordance with another aspect of the invention, an ECG analysis program is disclosed which, when executed, causes a processor to acquire ECG data from a patient, determine whether the patient is in one of a prespecified group, and if so, applies analysis criteria specific for the prespecified group to identify if the patient has an ACS. If the patient is not in a prespecified group, the program applies known analysis criteria to the ECG data. The group is specified based on gender, age, race, weight, height, or a combination thereof. The analysis includes modifying various parameters based on the specific group selected.

In accordance with another aspect of the invention, a method and apparatus, that includes an ECG device, is disclosed. The method is a criterion based, group membership-specific ACS detection method. The method includes specifying a group membership designated as having differing ECG data as compared to a baseline group, acquiring ECG data from a patient experiencing ACS symptoms, and then analyzing the ECG data based on group membership. The steps of the method are programmed into a processing unit of an ECG device having a plurality of lead wires to acquire the ECG data from the patient.

In a preferred embodiment, the specified group is females under the age of 60 and the ECG data includes lowering the ST segment, checking ST depression level in reciprocal leads and T wave thresholds so as to more accurately identify acute anterior myocardial infarction (MI) and acute inferior MI in younger females. This gender and age specific ACS criteria improve the sensitivity while maintaining high specificity and overall accuracy of acute ACS detection for female patients, especially those under the age of 60.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 5 is a low level flow chart showing a specific embodiment of the invention.

DETAILED DESCRIPTION OF THE PREFERRED EMBODIMENT

Figure 1:
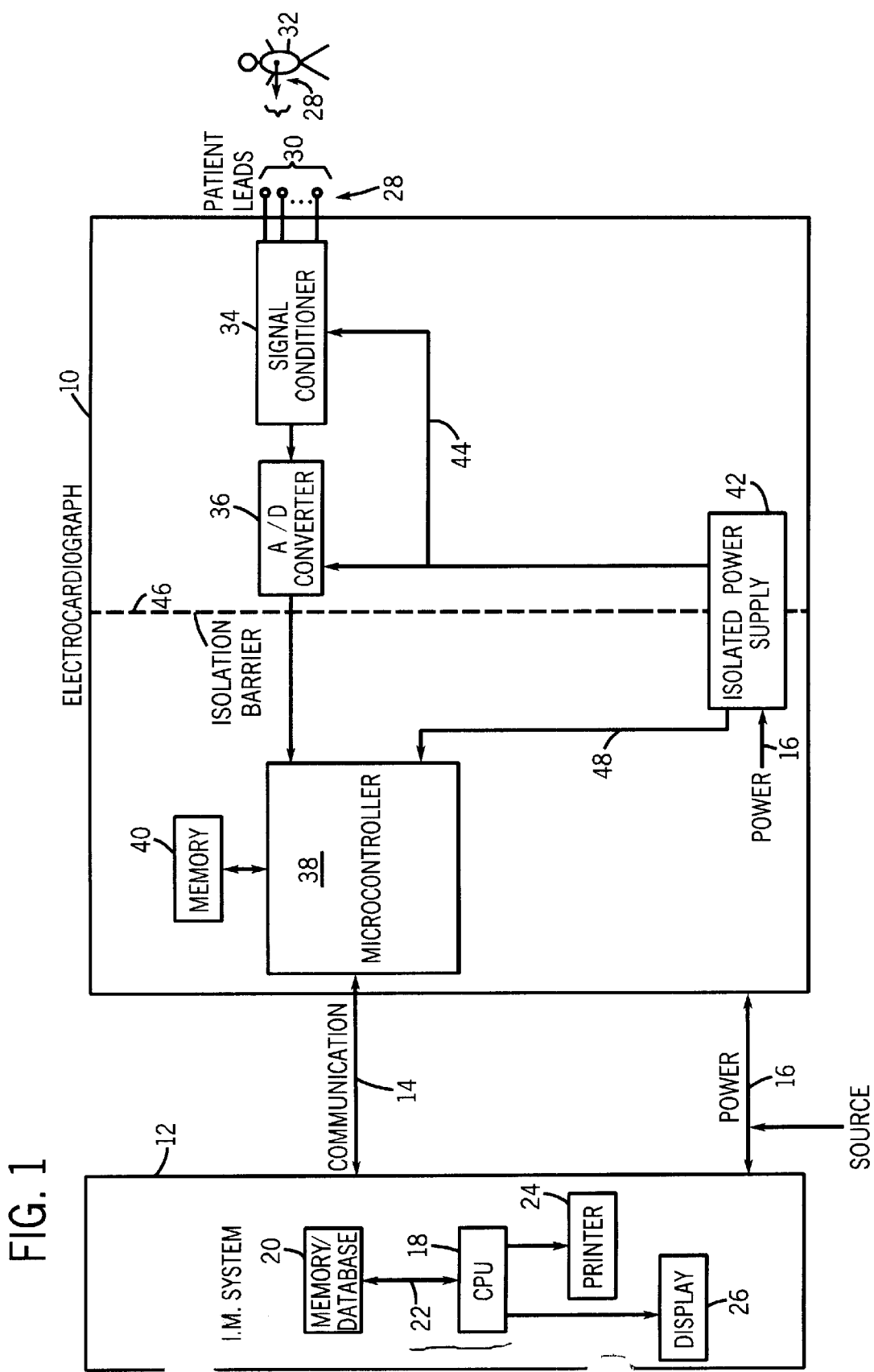
FIG. 1 is a block diagram of an electrocardiogram device connected to an information management system incorporating the present invention.

Referring to FIG. 1, an electrocardiogram device 10, in accordance with the present invention, is shown optionally connected to an information management system 12 through a communications link 14. A commonly used device for acquiring an ECG is a 12-lead electrocardiograph, such as the GE Marquette's MAC-5000 and a commonly used ECG analysis program is 12-lead ECG analysis program, such as GE-Marquette's 12SL™. The ECG device 10 and the information management system 12 receives power 16 from an external source. Among other things, the information management system 12 includes a central processing unit 18 connected to a memory unit, or database, 20 via a data link 22. The memory unit 20 may be RAM, ROM, a mass storage unit, a floppy disk, or any other computer readable storage medium, or a combination thereof. The CPU 18 processes data and is connected to an output, such as printer 24 and/or display 26. Alternatively, the electrocardiogram 10 can be connected directly to a printer 24 or display 26 through communications link 14 if the optional information management system 12 is not utilized, or the printer 24 and/or display 26 can be constructed integrally with the ECG device 10. The software program of the present invention may reside in either the ECG device 10, the information management system 12, or another device associated to receive signals from the ECG device 10.

The ECG device 10 is connected to a plurality of patient lead wires 28, each having an electrode 30 to receive ECG signals from a patient 32 in a known manner. The ECG device 10 has a signal conditioner 34 that receives the ECG signals and filters noise, sets thresholds, segregating signals, and provides the appropriate number of ECG signals for the number of leads 28 to an A/D converter 36 which converts the analog signals to digital signals for processing by a microcontroller 38, or any other type of processing unit. Microcontroller 38 is connected to a memory unit 40, similar to memory unit 20, or any other computer readable storage medium. In a preferred embodiment, memory unit 40 is a combination of ROM and RAM, wherein the ROM is used for static data, such as computer programs, and the RAM is used for dynamic data, such as the ECG signals received from patient 32.

A power supply 42 is provided to supply isolated power 44 to the signal conditioner 34, the A/D converter 36, and any internal printer or display and provides an isolation barrier 46 to isolate the lead wires 28 from un-isolated power 48 and line voltage 16. Such electrical isolation is typically provided by a medical grade isolation transformer.

Figure 2:
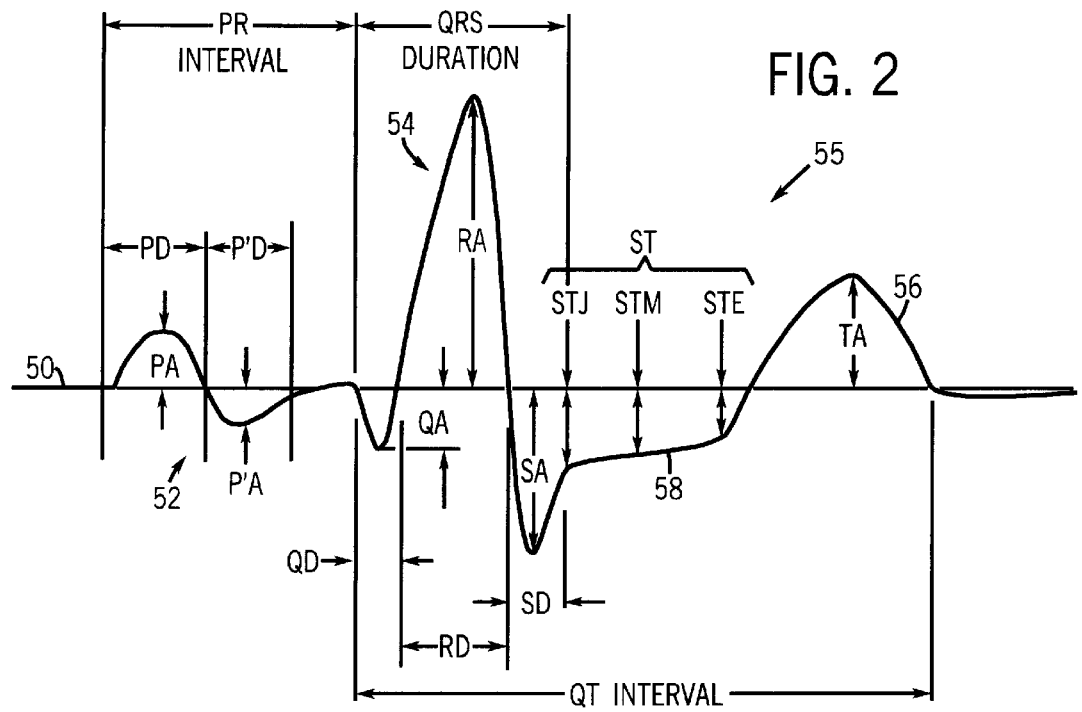
FIG. 2 is a timeline of one cardiac cycle of an ECG signal depicting the various wave components of interest to ECG analysis.

FIG. 2 shows one cardiac cycle of a typical ECG signal 50. The major components of the ECG signal 50 include the P-Wave 52, the QRS segment 54, and the T-Wave 56. Of particular interest in the present invention, is the ST segment 55 and the T-Wave 56. As is known, an elevated or depressed ST segment is an indication of acute myocardial infarction (MI), or acute cardiac ischemia (ACI), commonly known as unstable angina, both generically referred herein as acute cardiac syndromes (ACS). Another indication of ACS in the ECG signal 50 is an abnormal T-wave 56, such as an inverted T-Wave, a biphasic T-Wave, a hyperacute T-Wave, or a flat T-Wave. These ECG parameters are utilized herein in accordance with the present invention.

The present invention includes a method of developing automatic detection of ACS based on a particular patient type using these ECG signals. The method includes building a database of patients in which some have ACS and others do not, by retrospectively examining stored ECG databases from various medical facilities. The patient records selected are those in which the patients have a confirmed diagnosis of the presence or absence of an ACS using non-ECG diagnostic techniques. Using this database, the method next includes examining a difference of at least one ECG parameter for patients in a baseline group against patients in a second group that also includes patients having confirmed ACS and those not having ACS. In a preferred embodiment, a database is used to examine the difference of ST segment and T wave measurements between male and female ACS patients using statistical and pattern recognition methods.

As previously mentioned, the present invention is based on the fact that the conventional criteria for ECG ACS examination were carried out through ST measurements on a largely male dominated patient population or a population undifferentiated by gender, age, height, weight and/or race. By segregating the records of the second group, females in this case, from the baseline male-dominated group, and comparing the difference of ST segment and T wave measurements, a significance can be assigned to the ST segment and T wave differences. Since it was found that the difference in ST elevations was more significant for women under the age of 60, the technique is also preferably age limited. The technique next includes optimizing performance of ECG-based automatic detection of ACS for the second group of patients based upon the significance determined.

In a typical automatic detection routine for ACS, the ECG waveforms from the multi-lead electrocardiogram are provided to the microcontroller to first detect the ECG features, such as the P-waves, the QRS complexes, and the T-waves. This routine then generates a representative medium cardiac cycle for each lead, and then, generates lead by lead measurements of the ECG features. Cardiac rhythm analysis is then performed, as well as morphology analysis of the ECG features. The measurements and interpretation statements are then provided to the medical care provider. The present invention modifies the morphology analysis of the ECG features.

Figure 3:
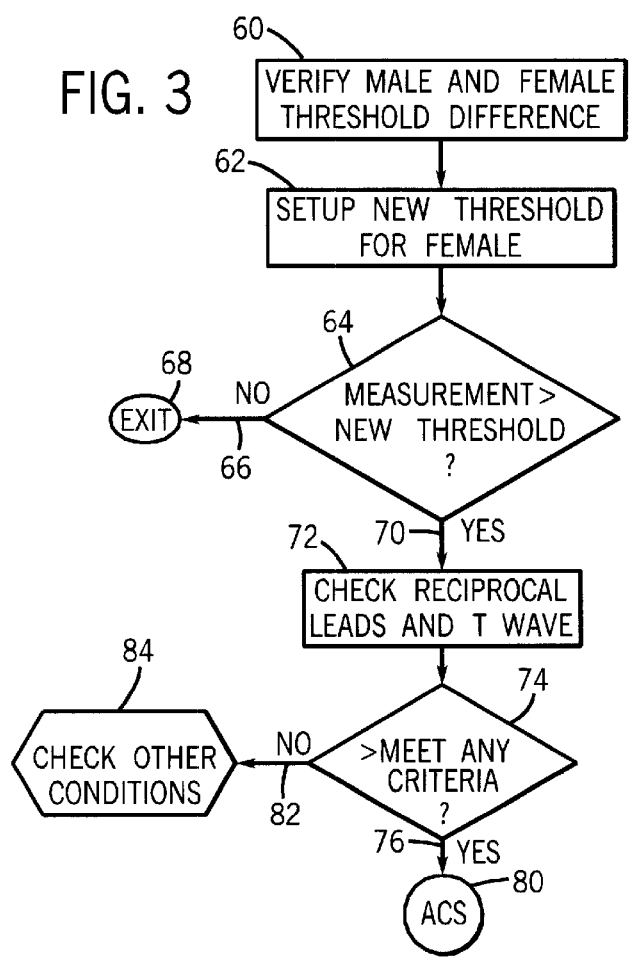
FIG. 3 is a high level flow chart depicting an algorithm and the method implemented in the apparatus of FIG. 1.

FIG. 3 is a high level flow chart of a preferred implementation of the present invention. After verifying an ECG parameter threshold difference between the two groups 60, which in the preferred embodiment is gender- and age-based, a new threshold is set for females under 60 years of age at 62. If the ECG parameter measurement is not greater than the new threshold level 64, 66, there is no ACS condition in this particular patient and the algorithm exits this subroutine at 68. In a preferred embodiment, the ECG parameters at issue are the ST elevation and T wave voltage. If the ST elevation is greater than the new threshold 64, 70 the reciprocal leads and the T-Wave are checked at 72 and if certain criteria for those parameters are met 74, 76, the system outputs an ACS alert 80. However, if the ST elevation is greater than the threshold 64, 70, but the specified criteria are not met 74, 82, the healthcare provider is advised to check for other possible causes 84.

Figure 4:
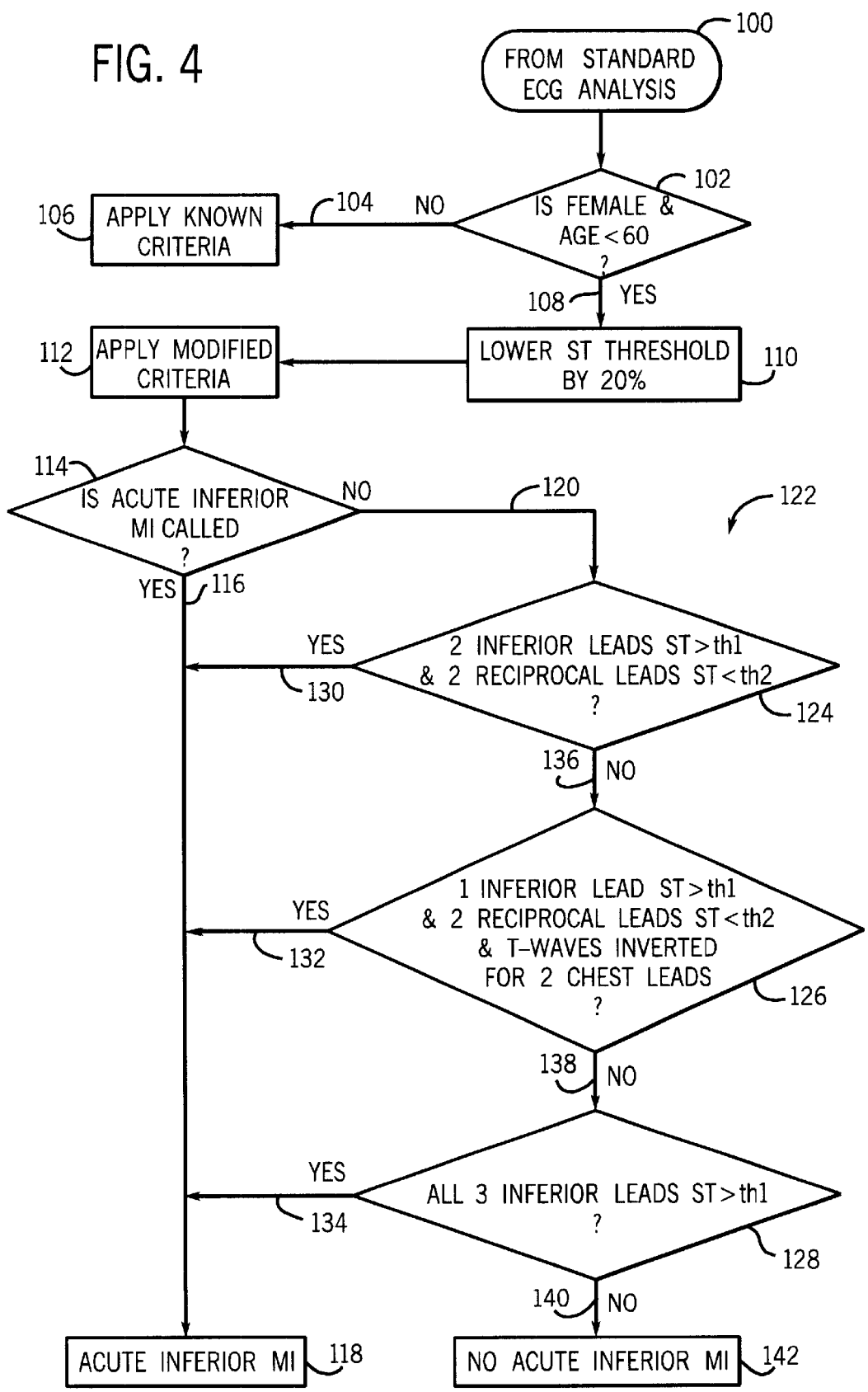
FIG. 4 is a low level flow chart showing a specific embodiment of the invention.

FIGS. 4 and 5 show specific embodiments of the present invention. FIG. 4 is a subroutine to determine acute inferior MI, whereas FIG. 5 shows a subroutine demonstrating the criteria to determine acute anterior MI. One skilled in the art will readily recognize that the implementation demonstrated in FIGS. 4 and 5 can be extended to the posterior and lateral diagnostic positions, as well as to other acute ischemia diagnoses.

Referring now to FIG. 4, a specific embodiment of the present invention is shown in detail. After the standard ECG analysis is implemented 100, the patient's gender and age are checked at 102. If the patient is not female or under the age of 60 104 the standard, known criteria are applied at 106 to continue the ECG analysis. However, if the patient is female and under the age of 60 at 102, 108, the ST segment threshold is decreased by 20% at 110. The known criteria are then modified accordingly and applied at 112, and if the modified criteria call for an acute inferior myocardial infarction (MI) directly 114, 116 the system immediately provides an acute inferior MI output at 118. If however, after applying the modified criteria 112, there is no indication of acute inferior MI or it is inconclusive 114, 120 a new set of criteria 122 is applied.

The new set of criteria 122 includes three distinct conditions 124, 126, and 128, and if any of the conditions provides a positive result 130, 132, 134, the ECG device outputs an acute inferior MI warning at 118. More specifically, if the ST measurement from at least two inferior leads is greater than a first ST threshold and the ST measurement from at least two reciprocal leads is less than a second ST threshold 124, 130, the acute inferior MI alert is output at 118. If not 124, 136, the next set of criteria is checked at 126. That is, if the ST measurement from at least one inferior lead is greater than the first ST threshold and the ST measurement from at least two reciprocal leads is less than the second ST threshold and at least two chest leads, or "V leads", indicate an inverted T-wave 126, 132, the acute inferior MI warning is produced at 118. If neither of the first two criteria are met 136, 138, the third set of criteria is checked 128. The third set of criteria 128 requires the ST measurement from all three inferior leads to be greater than the first ST threshold to produce the acute inferior MI warning 134, 118. If none of the criteria are met 136, 138, and 140 only then is a negative inferior MI result created and displayed 142.

Referring now to FIG. 5, an algorithm is depicted showing the present invention applied to acute anterior myocardial infarction (MI) analysis. After this subroutine is called from the standard ECG analysis 150, the patient's gender and age are checked at 152. If the patient is not female, or is female and over the age of sixty, 152, 154, the known criteria for acute anterior MI are applied at 156. However, if the patient is female and under the age of 60 at 152, 158, the ST threshold is decreased by 20% at 160 and the known criteria are modified and applied at 162. If the modified criteria indicate the presence of acute anterior MI 164, 166, the ECG device displays an acute anterior MI warning 168. However, if after applying the modified criteria 162, there is no indication of an acute anterior MI 164, 170, or is inconclusive, the analysis a new set of criteria is applied 172. The new set of criteria 172 includes at least three separate sets of criteria 174, 176, and 178. If any of these criteria are met 180, 182, or 184, the acute anterior MI warning is generated at 168. More particularly, the first set of criteria 174 includes checking if the ST measurement from at least two anterior leads is greater than the first ST threshold and if the ST measurement from at least one reciprocal lead is less than a second ST threshold 174, 180, the acute anterior MI warning is output at 168. If the first set of criteria is negative 174, 186, then the second set of criteria is checked at 176. The second set of criteria will be satisfied if the ST measurement from one interior lead is greater than the first threshold and the ST measurement from at least two reciprocal leads is less than the second ST threshold and at least one chest lead indicates an inverted T-wave 176, 182, which will then result in the acute anterior MI output 168. If the first two criteria are negative 186, 188, the third set of criteria is executed at 178. These criteria will set a warning for an acute anterior MI 184, 168 if the ST measurement from at least one anterior lead is greater than the first ST threshold and the ST measurement from at least two reciprocal leads is less than the second ST threshold. If none of the new criteria 172 are satisfied 186, 188, and 190, the ECG device indicates that the condition is negative for acute anterior MI 192.

Accordingly, the present invention includes a criterion based, gender acute cardiac syndrome detection method that includes acquiring patient specific data including specifying a group membership designated as having differing ECG data as compared to a baseline group and acquiring ECG data from a patient experiencing ACS symptoms. The criterion based method next includes analyzing the ECG data based on the group membership. In a preferred embodiment, the baseline group is male dominated and the second group includes females under the age of 60. However, one skilled in the art will recognize that other groups may similarly be affected and of the application of such other group is well within the scope of the present invention. For example, although the preferred embodiment is gender and age specific, other groups may include race specific, gender only specific, age only specific, weight only specific, height only specific or any combination thereof.

The invention also includes an ECG analysis program residing in computer readable memory 20, 40 capable of causing a processor 18, 38, when executed, to acquire ECG data from a patient and accept an input to determine whether the patient is in a prespecified group. If the patient is in a prespecified group, the program applies analysis criteria specific for the prespecified group to identify an ACS. If the patient is not in one of the prespecified groups, the known analysis criteria are applied. Threshold parameters are modified and a set of known criteria can be modified accordingly. Additionally, new sets of criteria can also be applied.

The aforementioned process and program can be implemented in an ECG device having a plurality of patient lead wires to acquire ECG data from a patient. The ECG device includes a processing unit connected to the plurality of patient lead wires to receive the ECG data and process the ECG data. The processing unit is also programmed to acquire patient specific data and ECG data from the patient. The ECG data is then analyzed as previously set forth.

The present invention has been described in terms of the preferred embodiment, and it is recognized that equivalents, alternatives, and modifications, aside from those expressly stated, are possible and within the scope of the appending claims.

What is claimed is:

1. A method of developing automatic detection of acute cardiac syndromes (ACS) based on a patient-type using ECG signals comprises the steps of:

examining a difference of at least one ECG parameter from patients in a baseline group that includes patients having ACS and those not having ACS, with patients in a second group that includes patients having ACS and those not having ACS;

determining a significance of the differences examined; and optimizing performance of ECG-based automatic detection of ACS for the second group of patients based on the significance determined.

2. The method of claim 1 further comprising the step of determining a quantitative value for a threshold of the ECG parameter specific to the second group.

3. The method of claim 1 wherein the second group of patients is selected from within at least one of the following groups: a gender-specified group, an age-specified group, a race-specified group, a weight-specific group, a height-specific group and a combination thereof.

4. The method of claim 1 further comprising the step of retrospectively examining ECG charts stored in databases of various hospitals, wherein each patient has a non-ECG diagnosis confirming a presence or absence of ACS.

5. The method of claim 1 wherein the baseline group is primarily male dominated and the second group is female dominated.

6. The method of claim 5 wherein the second group is age limited.

7. The method of claim 1 wherein the ECG parameter is ST elevation.

8. An ECG analysis program residing in computer readable memory capable of causing a processor, when executed to:

acquire ECG data from a patient;

determine whether the patient is in a prespecified group; and if so, apply analysis criteria specific for the prespecified group to identify an ACS group; and if the patient is not in a prespecified group, apply known analysis criteria.

9. The ECG analysis program of claim 8 wherein the processor is further caused to modify the known analysis criteria based on the specified group determined.

10. The ECG analysis program of claim 8 wherein the prespecified group is selected from within at least one of a gender-specified group, an age-specified group, a race-specified group, a weight-specific group, a height-specific group and a combination thereof.

11. The ECG analysis program of claim 8 wherein the prespecified group includes females under an age of 60.

12. The ECG analysis program of claim 8 wherein the ECG data include an ST segment and T wave measurements and the processor is further caused to modify ST and T wave thresholds.

13. The ECG analysis program of claim 12 wherein the ST threshold is lowered by 20%.

14. The ECG analysis program of claim 12 wherein program identifies whether the ACS is acute inferior myocardial infarction if any of the following criteria are present:

(1) the ST measurement from at least 2 inferior leads is greater than a first ST threshold and the ST measurement from at least 2 reciprocal leads is less than a second ST threshold;

(2) the ST measurement from an inferior lead is greater than the first ST threshold and the ST measurement from at least two reciprocal leads is less than the second ST threshold and at least 2 chest leads indicate an inverted T-wave; and (3) the ST measurement from at least three inferior leads is greater than the first ST threshold.

15. The ECG analysis program of claim 12 wherein the program identifies whether the ACS is acute anterior myocardial infarction if any of the following criteria are present:

(1) the ST measurement from at least 2 anterior leads is greater than a first ST threshold and the ST measurement from at least 1 reciprocal lead is less than a second ST threshold;

(2) the ST measurement from an anterior lead is greater than the first ST threshold and the ST measurement from at least two reciprocal leads is less than the second ST threshold and at least 1 chest lead indicates an inverted T-wave; and (3) the ST measurement from at least one anterior lead is greater than the first ST threshold and the ST measurement from at least two reciprocal leads is less than the second ST threshold.

16. The ECG analysis program of claim 8 wherein the program identifies whether the patient has an ACS and whether the ACS is acute anterior myocardial infarction or acute inferior myocardial infarction.

17. A criterion-based group membership specific acute cardiac syndrome (ACS) detection method comprising:

acquiring patient specific data including specifying a group membership designated as having differing ECG data as compared to a baseline group;

acquiring ECG data from a patient experiencing ACS symptoms;

analyzing the ECG data based on the specified group membership;

wherein the specified group membership is selected from at least one of: a gender-specified group, an age-specified group, a race-specified group, a weight-specific group, height-specific group, and a combination thereof; and modifying known analysis criteria based on the specified group membership.

18. The method of claim 17 wherein the specified group membership is females under an age of 60.

19. The method of claim 18 further comprising modifying an ST threshold if the specified group membership is females under an age of 60.

20. The method of claim 19 wherein the ST threshold is lowered by 20%.

21. The method of claim 17 further comprising identifying whether the patient has an ACS and whether the ACS is acute anterior myocardial infarction or acute inferior myocardial infarction.

22. The method of claim 21 wherein the ECG data includes an ST measurement and further includes identifying whether the ACS is inferior myocardial infarction if any of the following criteria are present:
   (1) the ST measurement from at least 2 inferior leads is greater than a first ST threshold and the ST measurement from at least 2 reciprocal leads is less than a second ST threshold;
   (2) the ST measurement from an inferior lead is greater than the first ST threshold and the ST measurement from at least two reciprocal leads is less than the second ST threshold and at least 2 chest leads indicate an inverted T-wave; and
   (3) the ST measurement from at least three inferior leads is greater than the first ST threshold.

23. The method of claim 21 wherein the ECG data includes an ST measurement and further includes identifying whether the ACS is acute myocardial infarction if any of the following criteria are present:
   (1) the ST measurement from at least 2 anterior leads is greater than a first ST threshold and the ST measurement from at least 1 reciprocal leads is less than a second ST threshold;
   (2) the ST measurement from an anterior lead is greater than the first ST threshold and the ST measurement from at least two reciprocal leads is less than the second ST threshold and at least 1 chest lead indicates an inverted T-wave; and
   (3) the ST measurement from at least one anterior lead is greater than the first ST threshold and the ST measurement from at least two reciprocal leads is less than the second ST threshold.

24. An ECG device comprising:
   a plurality of patient lead wires to acquire ECG data from a patient;
   a processing unit connected to the plurality of patient lead wires to receive and process the ECG data, the processing unit programmed to:
      acquire patient specific data including specifying a group membership designated as having differing ECG data as compared to a baseline group;
      acquire ECG data from a patient experiencing ACS symptoms; and
      analyze the ECG data based on the specified group membership
      wherein the processing unit is further programmed to modify known analysis criteria based on the specified group membership.

25. The ECG device of claim 24 wherein the specified group membership is selected from at least one of: a gender-specified group, an age-specified group, a race-specified group, a weight-specific group, height-specific group, and a combination thereof.

26. The ECG device of claim 24 wherein the specified group membership is females under an age of 60 and wherein the processing unit is further programmed to lower an ST threshold by approximately 20% if the specified group membership is females under an age of 60.

27. The ECG device of claim 24 wherein the ECG data includes an ST measurement and wherein the processing unit is programmed to identify whether the ACS is acute inferior myocardial infarction if any of the following criteria are present:
   (1) the ST measurement from at least 2 inferior leads is greater than a first ST threshold and the ST measurement from at least 2 reciprocal leads is less than a second ST threshold;
   (2) the ST measurement from an inferior lead is greater than the first ST threshold and the ST measurement from at least two reciprocal leads is less than the second ST threshold and at least 2 chest leads indicate an inverted T-wave; and
   (3) the ST measurement from at least three inferior leads is greater than the first ST threshold.

28. The ECG device of claim 24 wherein the ECG data includes an ST measurement and wherein the processing unit is further programmed to identify whether the ACS is acute anterior myocardial infarction if any of the following criteria are present:
   (1) the ST measurement from at least 2 anterior leads is greater than a first ST threshold and the ST measurement from at least 1 reciprocal leads is less than a second ST threshold;
   (2) the ST measurement from an anterior lead is greater than the first ST threshold and the ST measurement from at least two reciprocal leads is less than the second ST threshold and at least 1 chest lead indicates an inverted T-wave; and
   (3) the ST measurement from at least one anterior lead is greater than the first ST threshold and the ST measurement from at least two reciprocal leads is less than the second ST threshold.

29. A criterion-based group membership specific acute cardiac syndrome (ACS) detection method comprising:
   acquiring patient specific data including specifying a group membership designated as having differing ECG data as compared to a baseline group;
   acquiring ECG data from a patient experiencing ACS symptoms;
   analyzing the ECG data based on the specified group membership; and
   modifying an ST threshold if the specified group membership is females under an age of 60.

30. The method of clam 29 wherein the ST threshold is lowered by 20%.

31. A criterion-based group membership specific acute cardiac syndrome (ACS) detection method comprising:
   acquiring patient specific data including specifying a group membership designated as having differing ECG data as compared to a baseline group;
   acquiring ECG data from a patient experiencing ACS symptoms;
   analyzing the ECG data based on the specified group membership;

identifying whether the patient has an ACS and whether the ACS is acute anterior myocardial infarction or acute inferior myocardial infarction;

wherein the ECG data includes an ST measurement and further includes identifying whether the ACS is inferior myocardial infarction if any of the following criteria are present:
   (1) the ST measurement from at least 2 inferior leads is greater than a first ST threshold and the ST measurement from at least 2 reciprocal leads is less than a second ST threshold;
   (2) the ST measurement from an inferior lead is greater than the first ST threshold and the ST measurement from at least two reciprocal leads is less than the second ST threshold and at least 2 chest leads indicate an inverted T-wave; and
   (3) the ST measurement from at least three inferior leads is greater than the first ST threshold.

32. The method of claim 31 wherein the ECG data includes an ST measurement and further includes identifying whether the ACS is acute myocardial infarction if any of the following criteria are present:
   (1) the ST measurement from at least 2 anterior leads is greater than a first ST threshold and the ST measurement from at least 1 reciprocal leads is less than a second ST threshold;
   (2) the ST measurement from an anterior lead is greater than the first ST threshold and the ST measurement from at least two reciprocal leads is less than the second ST threshold and at least 1 chest lead indicates an inverted T-wave; and
   (3) the ST measurement from at least one anterior lead is greater than the first ST threshold and the ST measurement from at least two reciprocal leads is less than the second ST threshold.

33. An ECG device comprising:
   a plurality of patient lead wires to acquire ECG data from a patient;
   a processing unit connected to the plurality of patient lead wires to receive and process the ECG data, the processing unit programmed to:
      acquire patient specific data including specifying a group membership designated as having differing ECG data as compared to a baseline group;
      acquire ECG data from a patient experiencing ACS symptoms; and
      analyze the ECG data based on the specified group membership,
      wherein the specified group membership is females under an age of 60 and wherein the processing unit is further programmed to lower an ST threshold by approximately 20% if the specified group membership is females under an age of 60.

34. An ECG device comprising:
   a plurality of patient lead wires to acquire ECG data from a patient;
   a processing unit connected to the plurality of patient lead wires to receive and process the ECG data, the processing unit programmed to:
      acquire patient specific data including specifying a group membership designated as having differing ECG data as compared to a baseline group;
      acquire ECG data from a patient experiencing ACS symptoms;
      analyze the ECG data based on the specified group membership; and
      wherein the ECG data includes an ST measurement and wherein the processing unit is programmed to identify whether the ACS is acute inferior myocardial infarction if any of the following criteria are present:
         (1) the ST measurement from at least 2 inferior leads is greater than a first ST threshold and the ST measurement from at least 2 reciprocal leads is less than a second ST threshold;
         (2) the ST measurement from an inferior lead is greater than the first ST threshold and the ST measurement from at least two reciprocal leads is less than the second ST threshold and at least 2 chest leads indicate an inverted T-wave; and
         (3) the ST measurement from at least three inferior leads is greater than the first ST threshold.

35. An ECG device comprising:
   a plurality of patient lead wires to acquire ECG data from a patient;
   a processing unit connected to the plurality of patient lead wires to receive and process the ECG data, the processing unit programmed to:
      acquire patient specific data including specifying a group membership designated as having differing ECG data as compared to a baseline group;
      acquire ECG data from a patient experiencing ACS symptoms;
      analyze the ECG data based on the specified group membership; and
      wherein the ECG data includes an ST measurement and wherein the processing unit is further programmed to identify whether the ACS is acute anterior myocardial infarction if any of the following criteria are present:
         (1) the ST measurement from at least 2 anterior leads is greater than a first ST threshold and the ST measurement from at least 1 reciprocal leads is less than a second ST threshold;
         (2) the ST measurement from an anterior lead is greater than the first ST threshold and the ST measurement from at least two reciprocal leads is less than the second ST threshold and at least 1 chest lead indicates an inverted T-wave; and
         (3) the ST measurement from at least one anterior lead is greater than the first ST threshold and the ST measurement from at least two reciprocal leads is less than the second ST threshold.

* * * * *